US00PP10803P

United States Patent [19]

Craig

[11] Patent Number: Plant 10,803

[45] Date of Patent: Feb. 23, 1999

[54] REGAL PELARGONIUM PLANT NAMED 'DEBUTANTE'

[75] Inventor: Richard Craig, State College, Pa.

[73] Assignee: The Penn State Research Foundation, University Park, Pa.

[21] Appl. No.: 929,296

[22] Filed: Sep. 5, 1997

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Thomas J. Monahan

[57] ABSTRACT

The new cultivar maintains a controlled growth habit and is very heat tolerant. The petals are medium pink at the edges and white in the middle with a dark burgundy eye.

1 Drawing Sheet

BACKGROUND OF THE NEW PLANT

The present invention comprises a new and distinct cultivar of *Pelargonium×domesticum* known by the name 'Debutante' (Breeder No. 92-26-3). The new cultivar was discovered in an organized, scientifically designed breeding program at the Department of Horticulture, The Pennsylvania State University, University Park, Pa. on Mar. 26, 1992. The breeding program was designed to create new Regal Pelargonium cultivars with clear, bright flower colors, excellent propagation characteristics, compact growth habit, predictable and consistent flowering response and good post-harvest quality. The new cultivar is a selection from the crossing of the commercial cultivar 'Allure', U.S. Plant Pat. No. 7,467, and the commercial cultivar 'Fantasy', U.S. Plant Pat. No. 7,538. The new cultivar was first asexually reproduced by cuttings at The Pennsylvania State University and subsequently at Oglevee, Ltd., 152 Oglevee Lane, Connellsville, Pa. Trials were conducted over three years in the greenhouse plus garden trials. It has been found to retain its distinct characteristics through successive propagations.

The new cultivar exhibits a medium pink flower color distinct from the parentage and has better heat resistance than the parentage. The foliage and growth habit are intermediate between those of the parent plants.

The new cultivar, when grown in a glass greenhouse in Connellsville, Pa. using full light, 60° F. night temperature, 68° F. day temperature, and grown in a soilless media with constant fertilizer of 150–200 parts per million nitrogen and potassium, has a response time of fourteen weeks from a rooted cutting to a flowering plant in a 6 inch pot.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee, Ltd. in Connellsville, Pa. The plants were started as rooted cuttings which were potted on Nov. 4, 1994 and then flowered on Feb. 10, 1995. The plant histories were taken on plants blossomed under full light in a greenhouse and color readings were taken indoors under 200–220 foot candles of cool white fluorescent light. Color references are primarily to the R.H.S. Colour Chart of The Royal Horticultural Society of London.

The Plant

Classification:
- *Botanical.*—*Pelargonium×domesticum.*
- *Commercial.*—Regal Pelargonium named 'Debutante'.

Form: Upright mound.
Height: 21.0–23.0 cm from top of pot.
Growth: Quick rooting; medium vigor.
Strength: No artificial support needed.
Foliage: Stalked leaf attachment.
Leaves:
- *Size.*—5.0–7.0 cm across.
- *Shape.*—Depressed ovate; truncate base.
- *Margin.*—Serrately lobed.
- *Texture.*—Pubescent, leathery.
- *Color.*—Top: Green Group 138A. Bottom: Green Group 138B.
- *Ribs and veins.*—Venation: Palmate. Color: Green Group 138B.

Petioles:
- *Length.*—6.8–8.7 cm long.
- *Color.*—Yellow-Green Group 144A.

Stem:
- *Color.*—Green Group 143B.
- *Internodes.*—1.5–3.0 cm in length.

The Bud

Shape: Elongated, elliptical cluster.
Size: 2.0–4.0 cm across.

Inflorescence

Flowering habit: Large florets forming a full, continuous flower head.
Borne: Umbel; florets on pedicel; pedicel on peduncle.
Tonality from a distance: Medium pink outer petals with white towards centers. Prominent, dark eye on two petals. Dark stigma is striking against white center.
Size: 11.0–12.0 cm across fully opened inflorescence.
Closed Florets: 1.5–2.0 cm long; slightly showing color.
Open Florets:
- *Form.*—Cupped, ruffled.
- *Color.*—Top: Red-Purple Group 73B at edge to middle of petal. White Group 155D from middle to base of petal. Bottom: Red-Purple Group 73D. Eye: Visible only on upper two petals. At the darkest point center blotch, Greyed-Purple Group 187A, fading to Red-Purple Group 61D. Veining ranges between Red-Purple Group 59A and Red-Purple Group 61D.
- *Petals.*—5–6.
- *Size.*—5.5–6.0 cm across.

*Texture and appearance.*—Smooth, iridescent, velvety.

Pedicel:

*Length.*—3.5–4.0 cm long.

*Color.*—Yellow-Green Group 144A.

Peduncle:

*Length.*—6.5–8.0 cm long.

*Color.*—Yellow-Green Group 144A.

Disease resistance: No known unusual susceptibilities to disease.

Lasting quality: Slow to shatter; continuous flowering.

Reproductive Organs

Stamens:

*Anthers.*—5 mm in length.

*Filaments.*—14–16 mm in length; white-pale pink in color.

*Pollen color.*—Golden brown.

Pistils:

*Number.*—1.

*Length.*—1.5–2.1 cm.

*Stigma.*—5–7 parted; Red-Purple Group 59A.

*Style.*—1 cm in length.

Ovaries:

*Color.*—Yellow-Green Group 147D; pubescent. 6–7 mm in length; superior.

*Fruit.*—None observed.

General Characteristics

The 'Debutante' cultivar has a distinct medium pink flower with a dark burgundy blotch on the upper two petals and a very prominent white center. Cutting production and rooting time are improved over the cultivar 'Allure'. The neat plant habit and beautiful color creates a very pleasing finished pot plant for both the grower and the consumer.

I claim:

1. A new and distinct cultivar of Regal Pelargonium plant substantially as shown and described.

* * * * *

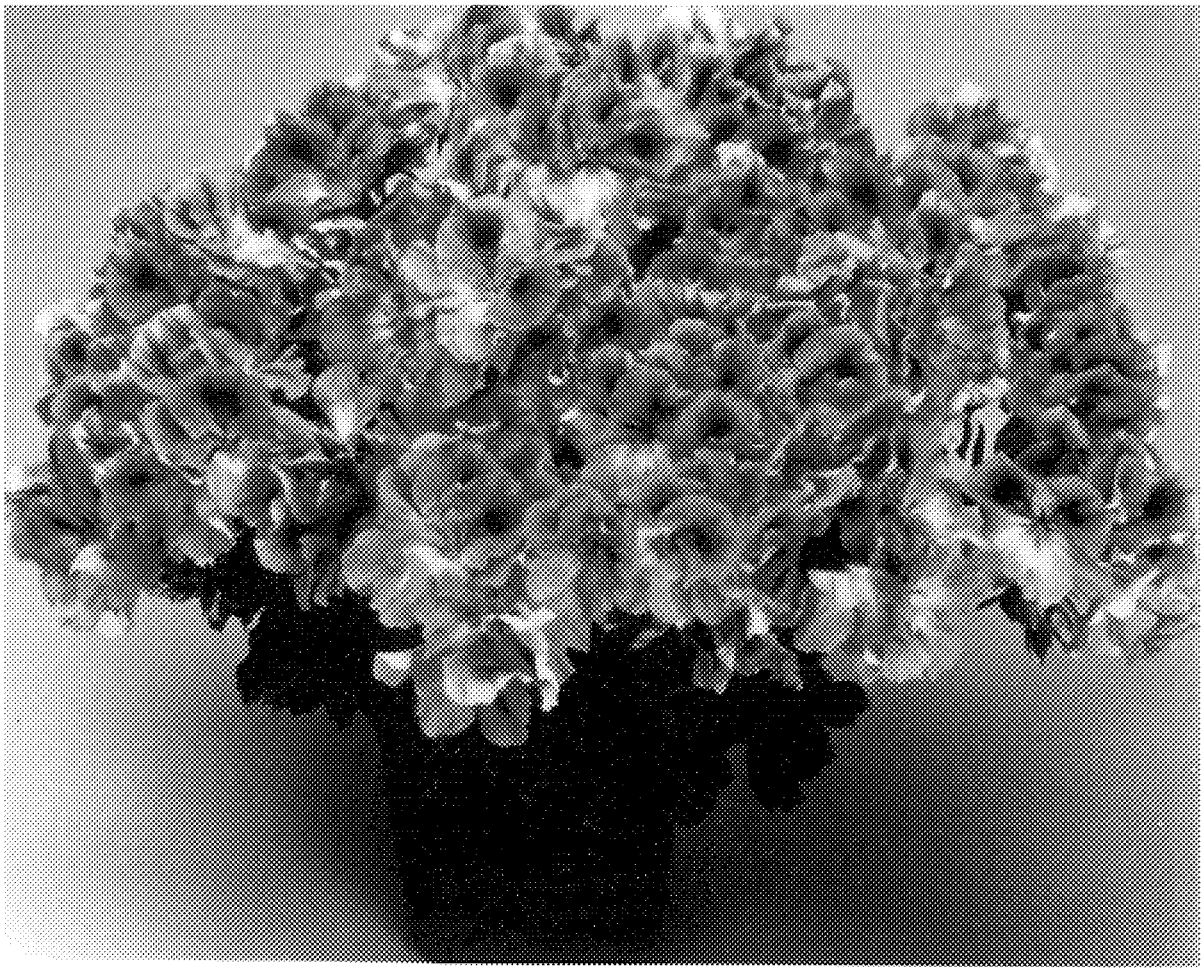

UNITED STATES PATENT AND TRADEMARK OFFICE

CERTIFICATE OF CORRECTION

PATENT NO. : PP 10,803
APPLICATION NO. : 08/929296
DATED : February 23, 1999
INVENTOR(S) : Richard Craig It is certified that error appears in the above-identified patent and that said Letters Patent is hereby corrected as shown below:

Title Page after the title, kindly insert the following:

--STATEMENT REGARDING FEDERALLY SPONSORED RESEARCH
This invention was made with government support under Hatch Act Project Nos. PEN03030 and PEN03393, awarded by the USDA. The Government has certain rights in the invention.--

Signed and Sealed this

Eighth Day of December, 2009

David J. Kappos

David J. Kappos
*Director of the United States Patent and Trademark Office*